(12) United States Patent
Salomon et al.

(10) Patent No.: US 7,715,901 B2
(45) Date of Patent: May 11, 2010

(54) SENSITIZED ONLINE BOLD-MRI IMAGING METHOD

(75) Inventors: Yoram Salomon, Rehovot (IL); Michal Neeman, Mazkeret Batya (IL); Avigdor Scherz, Rehovot (IL); Shimon Gross, Rehovot (IL); Assaf Gilead, Haifa (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 1083 days.

(21) Appl. No.: 10/513,656

(22) PCT Filed: May 8, 2003

(86) PCT No.: PCT/IL03/00371

§ 371 (c)(1),
(2), (4) Date: Jan. 20, 2006

(87) PCT Pub. No.: WO03/094695

PCT Pub. Date: Nov. 20, 2003

(65) Prior Publication Data

US 2006/0135868 A1 Jun. 22, 2006

Related U.S. Application Data

(60) Provisional application No. 60/378,409, filed on May 8, 2002.

(51) Int. Cl.
*A61B 5/05* (2006.01)
(52) U.S. Cl. .................. 600/411; 600/407; 600/410; 600/427; 600/431; 424/9.37; 424/9.4
(58) Field of Classification Search .............. 600/407, 600/410, 427, 411, 420, 431; 424/9.34, 9.37, 424/9.4
See application file for complete search history.

(56) References Cited

U.S. PATENT DOCUMENTS 5,159,065 A * 10/1992 Sessler et al. ............ 534/15
5,162,509 A * 11/1992 Sessler et al. ............ 534/15

(Continued)

OTHER PUBLICATIONS

Taylor; N. Jane, PhD, et al "BOLD MRI of Human Tumor Oxygenation During Carbogen Breathing" Journal of Magnetic Resonance Imaging, (2001) vol. 14, pp. 156-163.

(Continued)

*Primary Examiner*—Brian Casler
*Assistant Examiner*—Joel M Lamprecht
(74) *Attorney, Agent, or Firm*—Browdy and Neimark, PLLC

(57) ABSTRACT

An online Blood Oxygenation Level-Dependent (BOLD)-magnetic resonance imaging (MRI) method for functional clinical guidance or monitoring a therapeutic modality involving treatment by a sensitizer which, upon excitation by the appropriate sensitizing radiation, initiates local oxygen consumption, comprising: (i) generating a BOLD-weighted MR-image of the target region of interest within the patient's body (time $t_0$); (ii) administering said sensitizer to the patient; (iii) irradiating the target region while the patient is subjected to continuous MR imaging; (iv) generating a sole or a plurality of T2* weighted sequential BOLD MR-images during and/or after irradiation (time t); (v) processing the data generated at time $t_0$ and time t and generating a color-coded difference or ratio map on a pixel by pixel basis; and (vi) analyzing the processed data. The method is preferably applied to photodynamic therapy (PDT).

46 Claims, 10 Drawing Sheets

U.S. PATENT DOCUMENTS

| | | | | |
|---|---|---|---|---|
| 5,166,197 | A * | 11/1992 | Kenney et al. | 514/63 |
| 5,171,749 | A * | 12/1992 | Levy et al. | 514/410 |
| 5,177,073 | A * | 1/1993 | Gulliya et al. | 514/224.8 |
| 5,179,120 | A * | 1/1993 | Vogel et al. | 514/410 |
| 5,189,029 | A * | 2/1993 | Boyer et al. | 514/64 |
| 5,190,966 | A * | 3/1993 | Dougherty et al. | 514/410 |
| 5,214,036 | A * | 5/1993 | Allison et al. | 514/185 |
| 5,244,671 | A * | 9/1993 | Vogel et al. | 424/450 |
| 5,261,874 | A * | 11/1993 | Castle | 604/6.08 |
| 5,277,913 | A * | 1/1994 | Thompson et al. | 424/450 |
| 5,298,502 | A * | 3/1994 | Halling et al. | 514/185 |
| 5,888,997 | A | 3/1999 | Sessler et al. | |
| 6,022,959 | A | 2/2000 | Magda et al. | |
| 6,233,480 | B1 * | 5/2001 | Hochman et al. | 600/476 |
| 6,364,845 | B1 * | 4/2002 | Duffy et al. | 600/558 |
| 6,493,570 | B1 * | 12/2002 | Dees et al. | 600/411 |
| 6,567,684 | B1 | 5/2003 | Chenevert et al. | |
| 6,569,846 | B1 * | 5/2003 | Scherz et al. | 514/185 |
| 6,996,261 | B2 * | 2/2006 | deCharms | 382/131 |
| 7,097,825 | B2 * | 8/2006 | Gerber | 424/9.3 |
| 7,108,982 | B1 * | 9/2006 | Hageman | 435/7.1 |
| 2002/0099295 | A1 * | 7/2002 | Gil et al. | 600/476 |
| 2003/0017612 | A1 * | 1/2003 | Gerber | 436/173 |

OTHER PUBLICATIONS

Jordan, Benedicte F. et al "Changes in Tumor Oxygenation/Perfusion Induced by the No Donor, Isosorbide Dinitrate, in Comparison with Carbogen: Monitoring by EPR and MRI" Int. J. Radiation Oncology Biol. Phys., (2000) vol. 48, No. 2, pp. 565-570.

Abramovitch, Rinat et at "Analysis of Subcutaneous Angiogenesis by Gradient Echo Magnetic Resonance Imaging" MRM (1998) vol. 39, pp. 813-824.

Abramovitch, R et al "Stimulation of tumour angiogenesis by proximal wounds: spatial and temporal analysis by MRI" British Journal of Cancer (1998) vol. 77, No. 3, pp. 440-447.

Gilead, Assaf and Michal Neeman "Dynamic Remodeling of the Vascular Bed Precedes Tumor Growth: MLS Ovarian Carcinoma Spheroids Implanted in Nude Mice" Neoplasia (Aug. 1999) vol. 1, No. 3, pp. 226-230.

* cited by examiner

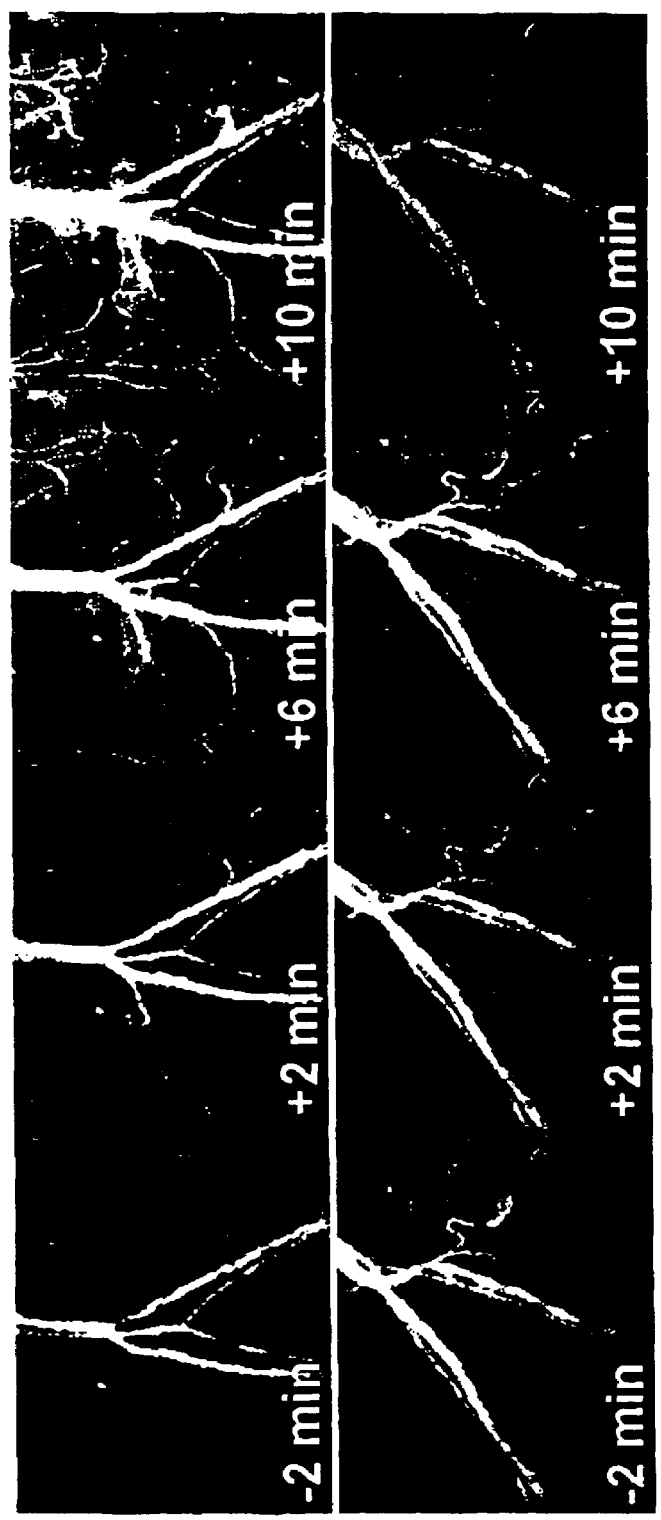

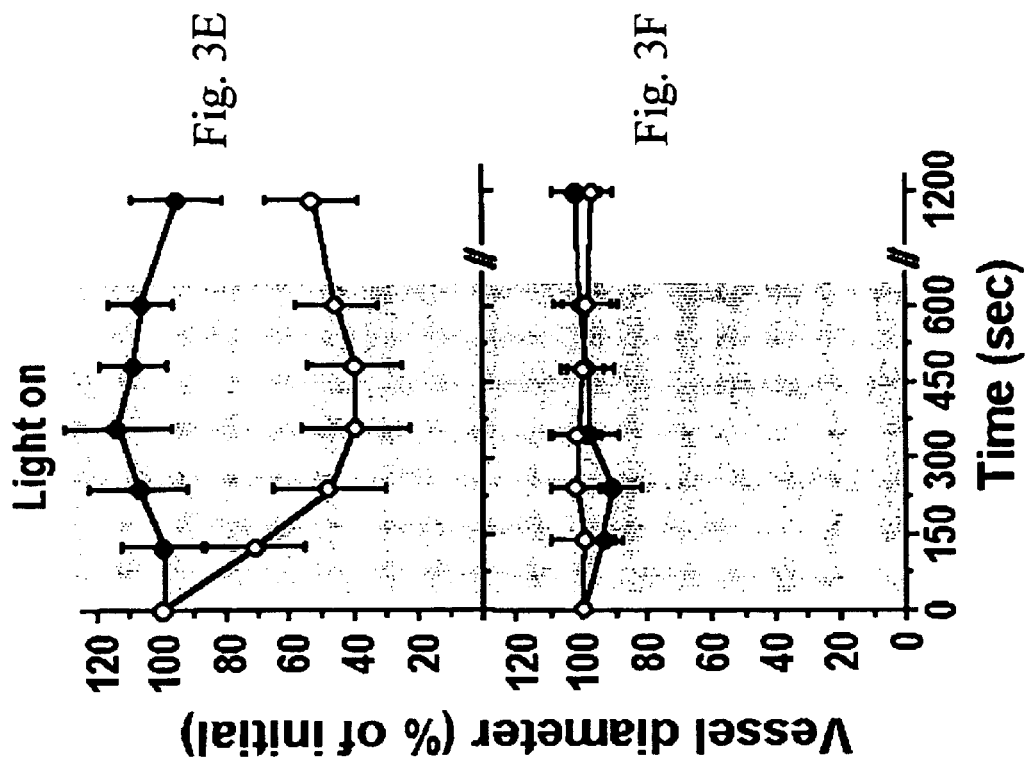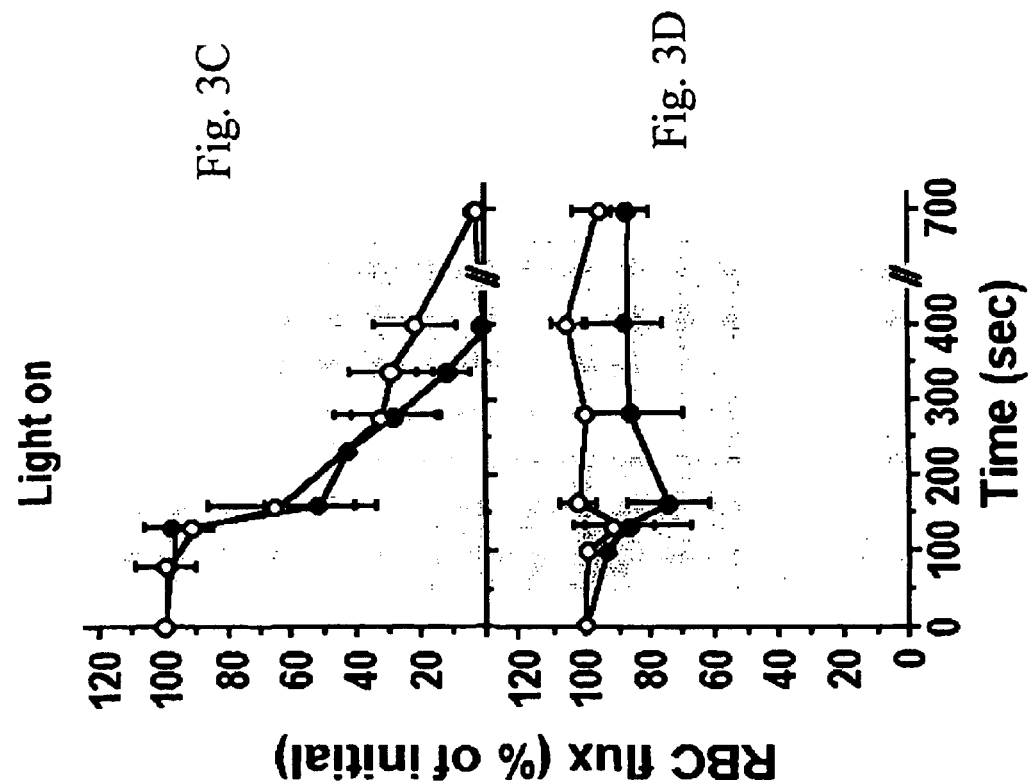

SENSITIZED ONLINE BOLD-MRI IMAGING METHOD

FIELD OF THE INVENTION

The present invention is in the field of clinical monitoring and guidance and relates to a magnetic resonance imaging (MRI) method based on the blood oxygenation level-dependent (BOLD) effect for this purpose, particularly in photodynamic therapy (PDT).

Abbreviations: Bchl: bacteriochlorophyll; BOLD: blood oxygenation level-dependent; Chl: chlorophyll; DLTI: drug-light time interval; fMRI: functional MRI; GE: gradient echo; Hb: hemoglobin; HNE: 4-hydroxynonenal; IHC: Immunohistochemistry; i.v.: intravenous; IVM: intravital microscopy; LPO: lipid peroxidation; MEGE: multiecho gradient echo; MR: magnetic resonance; MRI: magnetic resonance imaging; Pd-Bpheid: palladium-bacteriopheophorbide; PDT: photodynamic therapy; $pO_2$: oxygen partial pressure; PS: photosensitizer; RBC: red blood cels; ROS: reactive oxygen species; s.c.: subcutaneous; SI: signal intensity; $SPO_2$: hemoglobin saturation level; TRITC-dextran: tetramethyl rhodamine isothiocyanate-dextran; UV: ultraviolet.

BACKGROUND OF THE INVENTION

Photodynamic Therapy (PDT) relies on accumulation of an inactive photosensitizer (PS) drug in the tissue of interest followed by local illumination at the appropriate wavelength. The excited PS reacts in situ with molecular oxygen to produce highly cytotoxic reactive oxygen species (ROS) that lead to necrosis of the treated tissue. PDT represents a relatively new approach to cancer therapy such as lung, stomach, bladder, cervical, esophageal and skin cancers (Sibata et al., 2001; Hopper, 2000) and therapy of non-malignant diseases, e.g. alopecia, psoriasis, mesothelioma and menorrhagia (Dougherty, 2002), as well as in cardiology, for example in restenosis after angioplasty or atherosclerosis (Mansfield et al., 2001). and ophthalmologic diseases such as age-related macular degeneration (Fine, 1999).

A novel family of PSs derived from the photosynthetic pigments chlorophyll (Chl) and bacteriochlorophyll (Bchl), particularly from bacteriochlorophyll a (Bchla), has been recently synthesized in the laboratories of the present inventors for use in PDT, diagnostics and killing of cells or infectious agents in vitro upon illumination (Zilberstein et al., 2001; Rosenbach-Belkin et al, 1996; Gross et al., 1997; Schreiber et al., 2002; Koudinova et al 2003; U.S. Pat. No. 5,726,169; U.S. Pat. No. 5,955,585; U.S. Pat. No. 6,147,195; EP 0584552; WO 97/19081; WO 00/33833; WO 01/40232; and Israeli Patent Application No. 152900).

The lead compound from the novel family of PSs developed by the inventors, Pd-bacteriopheophorbide (Pd-Bpheid) (Schreiber et al., 2002; WO 00/33833), exhibits superior photochemical and pharmacological characteristics over clinically used PSs. Pd-Bpheid exhibits higher phototoxicity and photostability, faster clearance rates from the circulation with little or no damage to adjacent tissues, and strong absorption in the near infrared (760 nm) with $\Sigma_0 \sim 10^5$, enabling deeper photosensitization into the tumor tissue ~1.5 cm. Pd-Bpheid (Tookad®, Steba Biotech Ltd.) was tested in preclinical PDT treatment of normal canine prostate and shown to cause full necrosis of the tumor without functional urethral damage or damage to other adjacent tissues (Chen et al., 2002). Pd-Bpheid is now in advanced clinical trials for PDT of human prostate cancer.

Illumination of a tumor treated with bacteriochlorophyll-serine (Bchl-Ser), a PS described in EP 0584552, was shown by the present inventors to lead to light-dependent oxygen depletion (due to $O_2$ photoconsumption) (Zilberstein et al., 1997). Instant illumination following intravenous sensitizer administration (with no drug-light time interval (DLTI)) was shown to induce capillary occlusion, hemorrhage and blood stasis, resulting in tumor necrosis and eradication (Zilberstein et al., 2001). This novel anti-vascular treatment modality with Bchl-Ser or Pd-Bpheid was shown to induce high cure rates for melanoma, glioma, sarcoma and human prostate xenografts in mice (Zilberstein et al., 2001; Schreiber et al., 2002; Koudinova et al., 2003) and rats (Kelleher et al., 1999). PDT with Pd-Bpheid also decreased the incidence of metastasis, compared with conventional surgery (Schreiber et al., 2002). In studies performed with other sensitizers such as the chlorin-based photosensitizer MV6401 and the benzoporphyrin derivative verteporfin, similar hemodynamic alterations were related to short or no DLTI (Dolmans et al., 2002; Fingar et al., 1999; Pogue et al., 2001).

Precise light delivery is a prerequisite for accurate, efficient and safe PDT. While fiber insertion into internal organs can be assisted by various techniques such as optical, X-ray or ultrasound, real-time visualization of the light impact and tumor response is presently unavailable. The need for such a technique becomes critical in cases where the target tumor is internal, and/or located in the proximity of vital organs, nerves or major blood vessels. In such cases, it would be of advantage to enable imaging of the photosensitized treatment zone. Therefore, such an imaging technique will potentially enable higher treatment accuracy and safety, thus decreasing unwanted damage to neighboring non-diseased tissues.

Magnetic resonance imaging (MRI) can define human anatomy at a level of detail that cannot be achieved by any other medical imaging technique. In addition to depicting anatomy, MRI can evaluate tissue function. Recently, functional magnetic resonance imaging (fMRI) was developed as a technique for analysis of brain function (Detre and Floyd, 2001). fMRI enables detection and imaging of spatial and temporal changes in blood oxygenation, flow, and volume (Jordan et al., 2002) and includes blood oxygen level-dependent (BOLD) imaging, diffusion imaging, perfusion imaging, cerebrospinal fluid flow analysis and MR spectroscopy.

BOLD-MRI is an imaging protocol that is sensitive to specific relaxation rates which are influenced by deoxyhemoglobin. BOLD-MRI contrast is derived from the inherent paramagnetic contrast of deoxyhemoglobin using T2* weighted images (Howe et al., 2001; Turner, 1997). BOLD-MRI contrast was applied previously in cancer research for monitoring tumor response to vasomodulators (Jordan et al., 2000; Taylor et al., 2001), and by the present inventors for analysis of tumor vessel functionality, vessel maturation, and angiogenesis (Abramovitch et al., 1998 a, 1998b; Gilead and Neeman, 1999).

SUMMARY OF THE INVENTION

In accordance with the present invention, it was examined and found that oxygen photoconsumption and consequent hemodynamic effects, inherent to Pd-Bpheid-PDT, generate a change in the BOLD contrast and thus, that the BOLD-MRI technique can be used to evaluate the tumor vascular response during sensitizer-PDT in vivo.

The present invention thus provides an online Blood Oxygenation Level-Dependent (BOLD)-magnetic resonance imaging (MRI) method for functional clinical guidance or monitoring and follow-up of treatment progression of a therapeutic modality involving treatment by a sensitizer which, upon excitation by the appropriate sensitizing radiation, initiates local oxygen consumption or depletion, said method comprising:

(i) generating a BOLD weighted MR-image of the target region of interest within the patient's body (time $t_0$);

(ii) administering said sensitizer to the patient;

(iii) irradiating the target region of interest within the patient's body with the appropriate sensitizing radiation, while the patient is placed in the magnetic field of an MRI spectrometer and is subjected to continuous MR imaging;

(iv) generating a sole or a plurality of T2* weighted sequential BOLD MR images during and/or after irradiation (time t);

(v) processing the data generated at time $t_0$ and time t and generating a color-coded difference or ratio map on a pixel by pixel basis; and (vi) analyzing the processed data by displaying a composite image obtained by superimposing the map generated in (v) on the image generated in (i).

The therapeutic modality is preferably PDT.

DESCRIPTION OF THE FIGURES

FIGS. 2A, 2B and 2C (parallel adjacent sections of 2D, 2E and 2F, respectively) stained with hematoxylin-eosin. It can be noted that, at high magnification photographs of the viable region of the photodynamically-treated tumor (2A, 2D, ×400), HNE is confined to the blood/vessel interface while in the light-control tumor (2B, 2E), HNE is not observed. In the photodynamically-treated tumor at low magnification (2C, 2F, ×100), extensive PDT-dependent LPO in large vessels at the tumor rim can be observed. Positive HNE staining is also observed in the spontaneous necrotic core of the tumor (PDT independent). BV: blood vessel, VTR: viable tumor rim, NEC: necrosis.

FIGS. 3A-3G show that Pd-Bpheid PDT induced hemodynamic changes. Hemodynamic parameters were monitored by fluorescent intravital microscopy (IVM) in the mouse ear lobe. Blood vessels were pool-labeled with TRITC-dextran in (3A) PDT-treated and (3B) light-control animals. Images were taken at the indicated time points corresponding to onset of illumination. Red blood cell (RBC) flux was measured by video microscopy following i.v. administration of ~1% 4-Di-10-ASP, ex vivo stained RBC obtained from a donor mouse. RBC flux was measured in PDT-treated (3C, n=5) and light-control (3D, n=3) animals. Blood-vessel diameter was digitally measured from images like 3A, 3B in PDT-treated (3E, n=6) and light control (3F, n=4) animals. Results are represented as % of initial diameter. Open and solid circles represents RBC fluxes and vessel diameters as measured in arterioles and venules respectively. FIG. 3G show extravascular TRITC-dextran leakage, digitally measured from data as in 3A, 3B. Open triangles: PDT (n=6), solid triangles: light control (n=4). Results represents normalized macromolecular leakage (% of initial mean pixel intensity).

FIGS. 4A, 4B show representative experiments. FIG. 4C represents signal intensity (SI) average±SEM (n=3).

FIG. 5A is a photograph showing the experimental setup used for remote Pd-Bpheid administration and illumination of the mouse tumor inside the magnet. FIGS. 5B-5E are MR images: 5B, SC—PDT, 5D, 5E—light control. (5B, 5D) Anatomical (pre-PDT, GE) images, showing tumor location (T) and direction of sensitizing light beam (yellow arrows), (M) unilluminated muscle. (5C, 5E) BOLD-contrast MR signal intensity maps, superimposed on the corresponding anatomical images, at the indicated time points (min) relative to onset of illumination. Color-coded maps represent the logarithmic ratio of signal intensity over baseline. Note that reduction in signal intensity upon illumination of the Pd-Bpheid treated mouse (5C +4, +6 min) is solely confined to the illuminated tumor zone, while in the absence of Pd-Bpheid (5E) or light (unilluminated muscle marked M), no contrast is generated. Shown are representative experiments (PDT: n=6, light control: n=4).

DETAILED DESCRIPTION OF THE INVENTION

Figure 1:
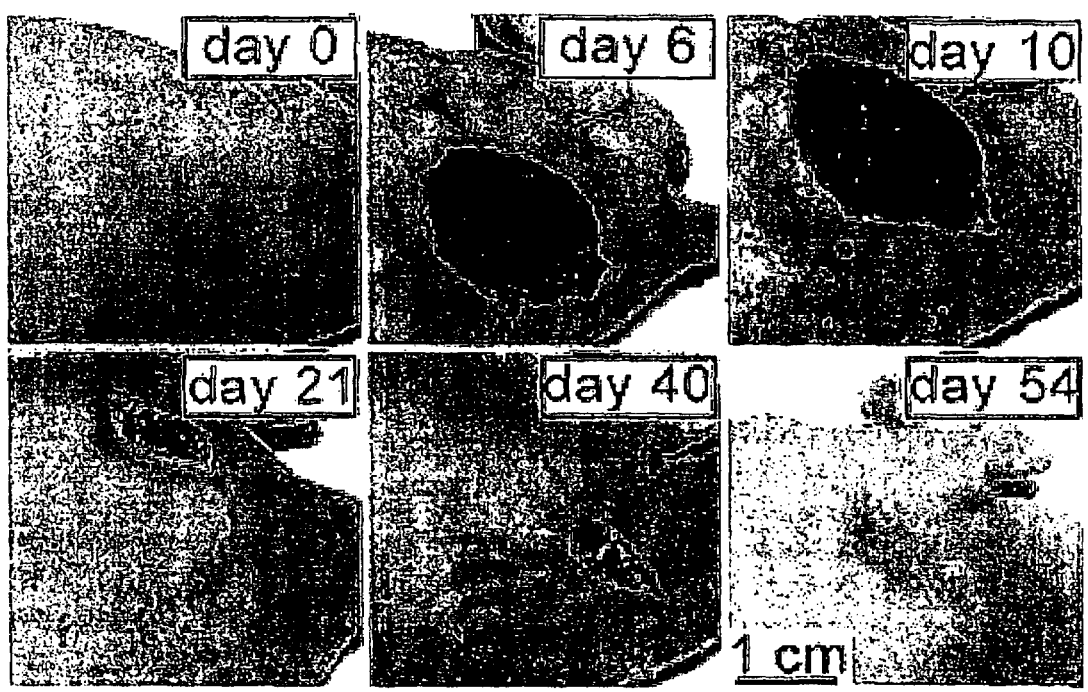
FIG. 1 depicts photographs of a mouse M2R melanoma tumor showing visual follow-up of the tumor before and after Pd-Bpheid PDT. A mouse bearing a s.c. M2R melanoma xenograft (8 mm) was treated with Pd-Bpheid (5 mg/kg, i.v) and light (763 nm, 102 J/cm$^2$) for 10 minutes). Photographs were taken before (day zero) and up to 54 days post treatment, when the mouse was considered cured. Severe necrotic lesion can be seen in the tumor area (days 6 and 10) followed by tissue remodeling (days 21 and 40), and cure (day 54).

Anti-vascular PDT relies on intravenous administration of a light-sensitive drug and immediate tumor illumination. In-situ generation of cytotoxic ROS with consequent O$_2$ photo-consumption (within seconds) leads to hemodynamic alterations, vascular shutdown (minutes), necrosis, and tumor eradication (days-weeks). The BOLD effect, generated by paramagnetic deoxyhemoglobin, forms the basis for functional MRI, traditionally used in neuroimaging.

The present invention is based on the fact that intravascular photosensitization leading to $O_2$ photoconsumption in course of PDT generates a measurable BOLD signal. Using Pd-Bpheid as a photosensitizer, a profound, instantaneous, light-dependent decrease (25-40%) in the MR signal intensity during PDT of M2R mouse melanoma xenografts is demonstrated herein according to the invention. Results were independently validated by IVM and IHC. These results indicate that BOLD-MRI is applicable for real-time, clinical monitoring of the tumor destructive process by PDT as well as for guided light delivery in PDT or other therapeutic modalities.

Thus, in one aspect, the present invention relates to an online BOLD-MRI method for functional clinical guidance or monitoring and follow-up of treatment progression of a therapeutic modality involving treatment by a sensitizer which, upon excitation by the appropriate sensitizing radiation, initiates local oxygen consumption or depletion, said method comprising:

(i) generating a BOLD weighted MR-image of the target region of interest within the patient's body (time $t_0$);

(ii) administering said sensitizer to the patient;

(iii) irradiating the target region of interest within the patient's body with the appropriate sensitizing radiation, while the patient is placed in the magnetic field of an MRI spectrometer and is subjected to continuous MR imaging;

(iv) generating a sole or a plurality of T2* weighted sequential BOLD MR images during and/or after irradiation (time t);

(v) processing the data generated at time $t_0$ and time t and generating a color-coded difference or ratio map on a pixel by pixel basis; and (vi) analyzing the processed data by displaying a composite image obtained by superimposing the map generated in (v) on the image generated in (i).

As used herein, the term "sensitizer" means a blood-borne or interstitial electromagnetic radiation-excitable agent which, upon excitation by the appropriate radiation, initiates local oxygen consumption or depletion. According to the present invention, the changes in the BOLD-MR contrast are generated by photoconsumption of oxygen resulting from sensitizer/irradiation-dependent in situ production of cytotoxic Reactive Oxygen Species (ROS) and/or by hemodynamic changes resulting from vascular insult induced by said ROS produced by the excited sensitizer in the region of interest. The oxygen consumption and/or hemodynamic insult result in alteration of paramagnetic deoxyhemoglobin content leading to changes in BOLD contrast.

Any therapeutic modality involving treatment with a sensitizer known today or to be discovered in the future can be used according to the invention. In a most preferred embodiment, the therapeutic modality is photodynamic therapy (PDT). In another embodiment, the therapeutic modality is X-ray based PDT (Kokotov et al., 1994).

According to the present invention, the therapeutic modality involving treatment by a sensitizer is preferably applied to a disease or disorder treatable with the sensitizer by local embolization or recanalization.

The term "disease or disorder treatable by local embolization" means a disease or disorder treatable by therapeutic introduction of a substance into a blood vessel in order to occlude it. These diseases or disorders may be a malignant disease such as solid tumors exemplified by, but not limited to, breast, prostate, kidney, colon, lung, stomach, bladder, uterus, cervical, ovarian, esophageal, brain or skin cancer. In preferred embodiments, the malignant disease is prostate, kidney, breast and skin cancer.

The disease or disorder treatable by local embolization may also be a non-malignant disease such as, but not limited to, psoriasis, rheumatoid arthritis, benign prostate hyperplasia, benign mesothelioma, menorrhagia, actinic keratosis (a precancerous disorder that about 20% of the cases develop into squamous cell carcinoma) or an ophthalmologic disease or disorder, particularly age-related macular degeneration (AMD).

The term "disease or disorder treatable by local recanalization" means a treatment leading to photodynamic reopening of previously occluded blood vessels. Examples are cardiovascular disorders such as, but not limited to, restenosis after angioplasty or atherosclerosis.

The term "region of interest" is the part within the patient's body being treated by the therapeutic modality, e.g. PDT. For example the region of interest may be a tumor region in the case of cancer, the macula in the case of age-related macular degeneration, and the site of restenosis.

In one preferred embodiment of the present invention, the sensitizer used in PDT is a photoactive dye (herein "photosensitizer") excitable by electromagnetic radiation selected from the group consisting of visible, infrared, near-infrared, and ultraviolet light (UV). In another embodiment, the sensitizer is a photosensitizer directly or indirectly excitable by ionizing radiation e.g. x-ray.

In one embodiment of the present invention, the photosensitizer is a photoactive dye used in PDT that, upon excitation by UV, visible, infrared or near-infrared light, catalyzes photoconversion of oxygen to local cytotoxic ROS.

The method of the present invention encompasses any photosensitizer known nowadays or in development or to be discovered in the future for use in PDT. Examples of such photosensitizers include porphyrin derivatives such as, but not limited to, Photofrin® (porfimer sodium, QLT Therapeutics) Foscan® (temoporfin, Biolitech Pharma Ltd.), Levulan® (ALA, 5-aminolevulinic acid, and derivatives thereof), Optrin® (Lutex, lutetium texaphyrin), talaporfin (taporfin sodium), Visudyne® (BPD, verteporfin, QLT Therapeutics) and other Chl and Bchl derivatives, including metal-substituted Chl and Bchl derivatives, disclosed for clinical use in therapy and diagnosis of tumors by PDT such as, but not being limited to, the Chl and Bchl derivatives described in U.S. Pat. No. 5,726,169; U.S. Pat. No. 5,955,585; U.S. Pat. No. 6,147,195; EP 0584552; WO 97/19081; WO 00/33833; WO 01/40232; and Israeli Patent Application No. 152900, all these patents and applications being hereby incorporated by reference in their entirety as if fully disclosed herein.

In one preferred embodiment of the present invention, the photosensitizer is a Bchl a derivative. In one most preferred embodiment, the photosensitizer is Palladium-bacteriopheophorbide (Pd-Bpheid) (Tookad®, Steba Biotech, France). In another preferred embodiment, the photosensitizer is the water-soluble palladium $3^1$-oxo-15-methoxycarbonylmethyl-rhodobacteriochlorin $13^1$-(2-sulfoethyl)amide potassium salt described in Israeli Patent Application No. 152900.

In yet another embodiment of the invention, the sensitizer is one that is indirectly excitable by x-rays or other ionizing radiation. One example of such sensitizer is the supramolecular assembly consisting of a water-dispersed polystyrene latex with an embedded scintillating compound, 2,5-diphenyloxazole, and an externally attached hematoporphyrin described by Kokotov et al., 1994.

The sensitizer can be administered to the patient interstitially or, more preferably, intravenously. In some cases, for particular efficiency or safety purposes, the sensitizer can be administered locally by injection or topical administration. For example, in restenosis after angioplasty, the sensitizer can be intravascularly released, upstream, adjacent to the treatment site, providing a higher local concentration of sensitizer. To achieve phtotdynamic activity the procedure is conducted under appropriate illumination/irradiation intravascularly administered via an optic fiber.

As mentioned in the Background section, BOLD contrast MRI was applied previously in cancer research for monitoring tumor responses to vasomodulators, but this is the first time that a change in BOLD contrast obtained by oxygen photoconsumption and consequent hemodynamic effects generated by a sensitizer excited by electromagnetic radiation, is applied for real-time, clinical monitoring/guidance of a therapeutic modality such as PDT.

Photosensitizers used in PDT of tumors may accumulate in the tumor cells and, upon irradiation, cause destruction of the tumor, or they are present in blood vessels or interstitial tissues around the tumor and, upon irradiation, cause vascular damage that leads to tumor necrosis, shrinkage and eradication. According to the present invention, the photosensitizer is one that is sensitized while in the blood vessels or interstitial tissues.

In the treatment of an ophthalmologic disease caused by neovascularization, such as age-related macular degeneration, one of the leading causes of blindness in the industrialized countries, PDT enables the possibility of occluding neovascular vessels using photochemical mechanisms. The photoactive dye, excitable by low intensity light, is administered to the patient and the target region of the eye is irradiated at the absorption peak of the dye. The mechanism of action consists of in situ generation of ROS with concomitant or subsequent photochemical reactions including peroxidation of lipids in endothelial cell membranes, which stimulate platelet adhesion and aggregation.

As used herein, the term "functional clinical guidance" means the interactive use of the information obtained by the online BOLD-MRI method for accurate delivery of irradiation to the target region of interest, e.g. the diseased region, within the patient's body. Consequently, these data can be used for monitoring and follow-up of treatment progression.

The changes in the BOLD-MRI contrast relate to the changes between the basal MR signal intensity in images taken prior to treatment and the MR signal intensity in images taken at discrete time points during and/or at the end of the treatment. For this purpose, according to standard MRI techniques, a BOLD weighted anatomical MR-image of the region of interest within the patient's body is generated before administration of the sensitizer to the patient ($t_0$), this baseline image showing tumor location. After administration of the sensitizer and subsequent irradiation of the diseased region containing the tumor, a sole or a plurality of T2* weighted sequential BOLD MR-images during and/or after irradiation (time t) is generated, for example at 4 and 6 min, or at 5, 10, 15 and 20 min, relative to onset of irradiation (time t). The data generated at time to and time t is processed thus generating a color-coded difference or ratio map on a pixel by pixel basis. Analysis of the processed data is obtained by superimposing the color-coded map generated by the processed data on the image generated at time $t_0$, thus displaying a composite image that will give the guidance for the physician performing the PDT. In the composite image, the areas showing a BOLD contrast effect due to the PDT treatment (identified by the coded color, e.g. red) should coincide with the tumor area.

In one embodiment of the invention, the online BOLD-MRI method can be performed intraoperatively for real-time assessment of tumor response to PDT, for example in course of brain tumor operation.

In another aspect of the present invention, the online BOLD-MRI method is performed for functional clinical guidance of PDT for pre-therapeutic imaging of the region of interest prior to the therapeutic treatment. In this case, the sensitizer is non-cytotoxic or is a cytotoxic agent used in a non-therapeutic sub-destructive dose such as to generate minimally destructive or toxic conditions in the region of interest. For this purpose, the sensitizer may be conjugated to a macromolecular carrier, preferably a physiologically inert high molecular weight macromolecule such as a polyaminoacid or a polysaccharide, whereby the sensitizer becomes cell-impermeable.

According to this aspect, the present invention provides a BOLD-MRI method for online imaging a diseased region within a patient's body for functional clinical guidance prior to a therapeutic treatment of a disease or disorder treatable by local embolization or recanalization, said treatment involving a blood-borne or interstitial electromagnetic radiation-excitable agent (herein designated "sensitizer") which, upon excitation by the appropriate radiation, initiates local oxygen consumption or depletion, which comprises administering to the patient subjected to continuous MR imaging while placed in the magnetic field of an MRI spectrometer, a non-therapeutic subtoxic dose of said sensitizer, irradiating the target diseased region with the appropriate sensitizing radiation, and analyzing the changes in the BOLD-MR contrast generated by oxygen consumption in response to excitation of the sensitizer in the diseased region by comparison with an MR-image of the diseased region generated before administration of the sensitizer.

The invention further provides a BOLD-MRI method for online imaging a diseased region of the body in the course of a therapeutic treatment of a disease or disorder treatable by local embolization or recanalization, said treatment involving a blood-borne or interstitial electromagnetic radiation-excitable agent (herein designated "sensitizer") which, upon excitation by the appropriate radiation initiates local oxygen consumption or depletion, which comprises administering to a patient subjected to continuous MR imaging while placed in the magnetic field of an MRI spectrometer, a therapeutic dose of said sensitizer, irradiating the target diseased region with the appropriate sensitizing radiation, and analyzing the changes in the BOLD-MR contrast generated by oxygen consumption in response to excitation of the sensitizer in the diseased region by comparison with an MR-image of the diseased region generated before administration of the sensitizer.

The invention will now be illustrated by the following non-limiting Examples and Figures.

EXAMPLES

Materials and Methods (i) Animals, tumor model and PDT Male CD1 nude mice (30 g±2 g) were implanted s.c. with M2R melanoma xenografts. PDT of anesthetized mice was performed on tumors (7-9 mm in diameter), as previously described (Zilberstein et al., 2001), with slight changes to allow for manipulation inside the magnet during MRI recording, or to perform PDT on the anesthetized mouse placed on the microscope stage during IVM. Intravenous (i.v.) Pd-Bpheid administration (5 mg/kg in vehicle, provided by Negma-Lerads Laboratoires, Toussus Le-Noble, France) was immediately followed by fiber optic guided tumor illumination (light spot Ø=1 cm$^2$, 763 nm, 102 J/cm$^2$) for 10 minutes, using a 1 W diode laser (CeramOptec GmbH, Bonn, Germany). The experiments were performed inside the magnet during the MRI recording (see details below). Room temperature was kept constant (28° C.) throughout the experiments.

Under these conditions, skin or tumor interstitial temperature (determined by a thermocouple) did not increase by more than 1° C. PDT was performed in three modes: (i) for tumor therapy, i.v. Pd-Bpheid administration was immediately followed by transcutaneous illumination; (ii) for MR imaging, Pd-Bpheid administration (by remotely activated i.v. catheterization) and transcutaneous illumination were performed inside the magnet (FIG. 5A); and (iii) for IVM, Pd-Bpheid administration and illumination of the semi-transparent mouse ear were conducted on top of the microscope stage.

Controls: Light control: illumination of tumors in mice administered with vehicle alone (without photosensitizer). Dark control, Pd-Bpheid administered to tumor-bearing mice without illumination. Mice were euthanized ($CO_2$) to avoid tumor burden when tumors reached ≧10% of body weight. All experiments were conducted according to institutional animal welfare regulations.

(ii) MRI Experiments.

(a) Gradient echo (GE) and multiecho gradient echo (MEGE) MR images were acquired on a horizontal 4.7 T Bruker Biospec spectrometer (Rheinstetten, Germany), as described previously (Gilead et al., 1999). Imaging parameters are as follows: slice thickness 0.8 mm, TR 230 ms, TE 10 ms for GE and TE 10, 21.24 and 32.48 ms for MEGE, flip angel 40°, acquisition (AQ) time 117 sec, matrix 256×256 pixels.

Figure 5A:
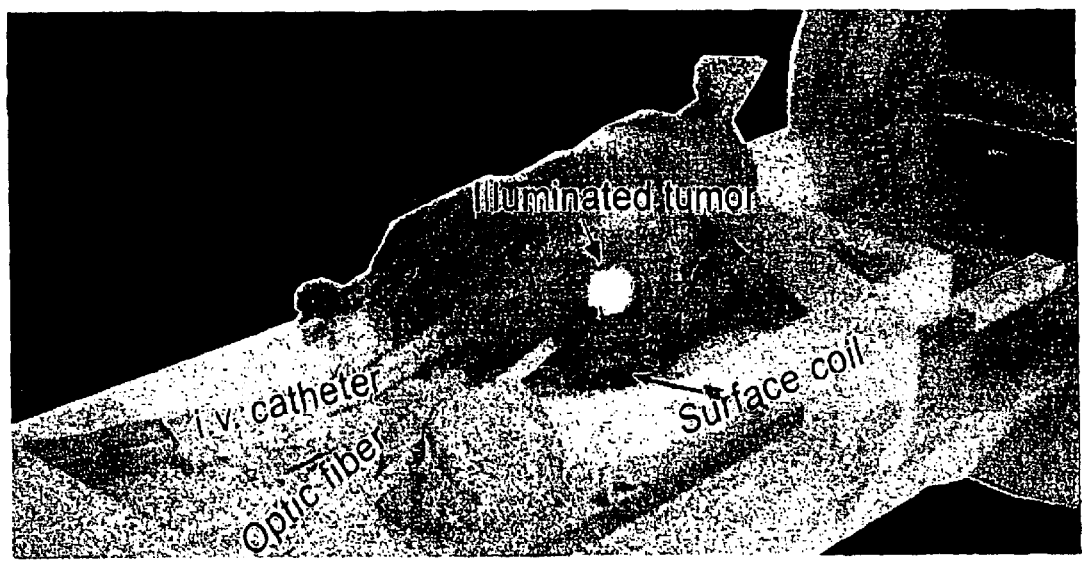
FIGS. 5A-5E are photographs showing online BOLD-MRI contrast of Pd-Bpheid-PDT of a mouse bearing a M2R melanoma tumor.
Figure 5B:
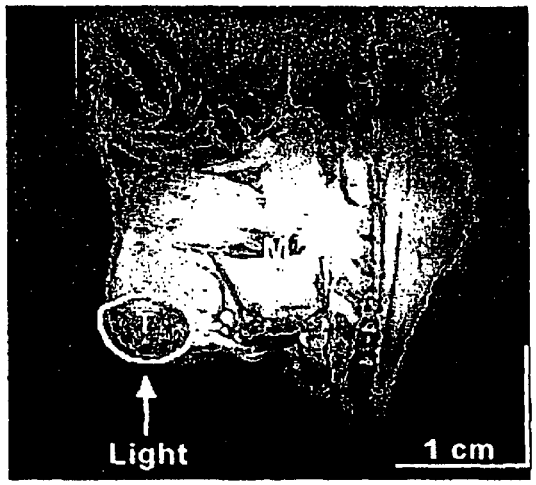

(b) Animal studies: Whole body excitation coil and an RF decoupled 1.5 cm surface coil were used for improving signal/noise ratio (field of view 4 cm, slice thickness 0.8 mm). Mice were anesthetized, catheterized, and restrained by adhesive tape (supine/lateral) to locate the tumor above the center of the MRI surface coil; the laser optic fiber was fixed in place to illuminate the tumor area (FIG. 5A). After four sequential images were acquired, mice were treated i.v. with Pd-Bpheid (5 mg/kg) followed by 10 min illumination, while 11 more images were acquired. Room temperature was maintained at 28° C.

(c) Ex-vivo measurements: Freshly collected human blood in sodium citrate was spun down and re-suspended in autologous plasma to 0.6-0.7 hematocrit to minimize red blood cell (RBC) sedimentation during MRI experiments. Blood samples (500 µl) were placed in 6×50 mm glass tubes (Kimble, Div. of Owens, Ill., USA), sealed under $N_2$ and each placed in a 3.5 ml optical plastic cuvette containing 2 ml of PBS. A proton volume coil was used (field of view 7 cm, slice thickness 2 mm, data was zero filled to matrix 512×512). Data were analyzed as the mean signal intensity of the blood sample relative to the surrounding phosphate-buffered saline (PBS).

(d) Data analysis: MRI data was analyzed using Matlab (The MathWorks Inc., Natick, Mass., USA), Orisis (Version 4.0.9, Geneva, Switzerland) and Paravision 2.1.1 (Bruker, Rheinstetten, Germany). MR signal intensity was derived from each image, either from the region of interest inside the tumor or in control tissue, and normalized to the first image. Response maps were generated by division of each image by the average of the first 2 pre-PDT images. R2* maps were derived by noise weighted linear regression of log(SI), for each pixel. Only pixels with fit of $R^2 \geq 0.36$ were analyzed. R2*: MRI relaxivity parameter; $R^2$: statistical correlation parameter.

(iii) Immunohistochemistry (IHC): Histological and immunohistological examinations were used for validation of the results obtained during the PDT experiments conducted by MRI and IVM. Dissected tumors were fixed in paraformaldehyde, and embedded in paraffin. IHC of PDT-induced LPO was based on immunodetection of HNE (4-hydroxynonenal), an aldehydic peroxidation product of polyunsaturated fatty acids that forms covalent adducts with proteins by reductive amination and/or Michael type addition (Uchida et al., 1995). PDT-damaged areas were visualized by IHC with anti-HNE. Thus, tumor sections were re-hydrated, blocked with bovine serum albumin for 4 h at 37° C., and treated with rabbit anti-HNE antiserum specifically recognizing HNE adducts (Calbiochem, La Jolla, Calif., USA, 1:400). HRP-conjugated goat anti-rabbit antibody served as 2$^{nd}$ antibody (Jackson, West Grove, Pa., USA) using 3-amino-9-ethylcarbazole as a chromogenic substrate (AEC, Sigma, St. Louis, Mo., USA).

sPO$_2$ of photosensitized blood: Optical spectroscopy. Fresh human blood collected in Na-citrate was steered (37° C.) in a sealed optical cuvette (under $N_2$) without or with Pd-Bpheid (100 µg/ml). Online spectroscopic sPO$_2$ determination was performed with a LESA reflectance spectrometer (Biospec, Moscow, Russia) as described (Neeman et al., 2001). Recording was initiated 2 minutes prior to illumination. Ten illumination cycles (1 min each, 170 mW/cm$^2$) were performed with spectral measurements (8×5 sec) in the intervening periods when the light was turned-off.

(iv) Intravital microscopy (IVM). Fluorescent IVM was performed with an upright microscope (Nikon Optiphot 2, Kawasaki, Japan) equipped with a thermoregulated stage (37° C.), a CCD camera (50 fps, Applitech, Tel-Aviv, Israel) and a VCR (JVC model HR-J437MS, Yokohama, Japan) for video recording.

Fluorescent IVM in the nude mouse ear lobe (Proske et al, 2000) was used for analysis of changes in vascular diameter, vascular permeability and blood flow. RBC from a donor mouse were labeled ex vivo with 4-(4-(didecylamino)styryl)-N-methylpyridinium iodide (4-Di-10-ASP, 7.5 µg/ml, Molecular Probes, Eugene, Oreg., USA), as previously described (Neeman et al., 2001). The labeled RBC mixed with TRITC-dextran (256 KDa, 0.5 mg/mouse as blood-pool marker, Sigma, St. Louis, Mo., USA) were i.v. administered to the tumor-bearing mouse (labeled cells comprised 1.17+/−0.08% of host RBC as verified on blood smears) and allowed to circulate for 10 min prior to video recording (mag. ×100, 20 min), starting 5 min prior to Pd-Bpheid/light and ending 5 min after the light was turned-off. Mice were euthanized by $CO_2$ at the end of the experiment.

Fluorescence images of blood vessels were acquired every 2 minutes, before, during and up to 10 minutes after illumination. Two hemodynamic parameters were digitally calculated (Scionimage software, Scion Corp., USA) from these images: (1) Changes in blood vessel diameter (arteriolar and venular), and (2) Extravascular leakage of TRITC-dextran (measured as changes in mean pixel intensity at an 2500 µm$^2$ extravascular region of interest). Both parameters are presented as % of initial value.

At the end of intravital recording, blood smears were prepared from the labeled RBC as well as from the treated-mouse peripheral blood. These smears were analyzed by fluorescence microscopy for determination of the labeled RBC fraction. A total of 2000 RBC were digitally counted in each experiment (Scionimage, Scion Corp., USA). The mean fraction of labeled RBC was found to be 1.17+/−0.08%.

EXAMPLE 1

Follow up of Tumor Response After PDT with Pd-Bpheid

Male CD1 nude mice, s.c. implanted with M2R melanoma xenografts were i.v.-injected with Pd-Bpheid (5 mg/kg) and instantly illuminated for 10 minutes (102 J/cm$^2$). Hemorrhagic tumor necrosis (10/11 mice within 24-48 h) was accompanied by a strong inflammatory response. Tumors in untreated (4/4) light (4/4 mice) or dark (4/4 mice) controls continued to grow reaching ≦10% of body volume by 9±3 days. Photographs of one mouse were taken before (day zero) and up to 54 days post-treatment, when the mouse was considered cured. As shown in FIG. 1, severe necrotic lesion can be noted in the tumor area (days 6 and 10), followed by tissue remodeling (days 21 and 40) and cure (day 54).

EXAMPLE 2

Vascular Photodamage

Figure 2C:
FIGS. 2A-2F are photographs showing immunohistochemistry (IHC—2D, 2E, 2F) of mouse M2R melanoma tumor following Pd-Bpheid PDT. Tumors were dissected one hour after PDT, fixed and prepared for IHC. Positive immunostaining of 4-hydroxynonenal (HNE)-protein adducts formed as a result of lipid peroxidation (LPO) at the tumor sites (brown colored, indicative for LPO) were observed following PDT (2D, 2F) but was negative in the light control (2E).
Figure 2F:
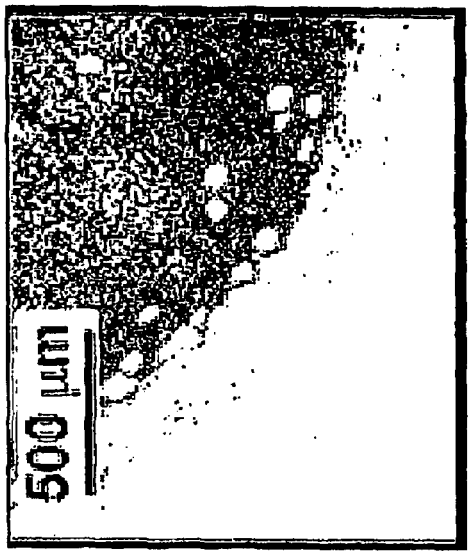
Figure 2B:
Figure 2E:
Figure 2A:
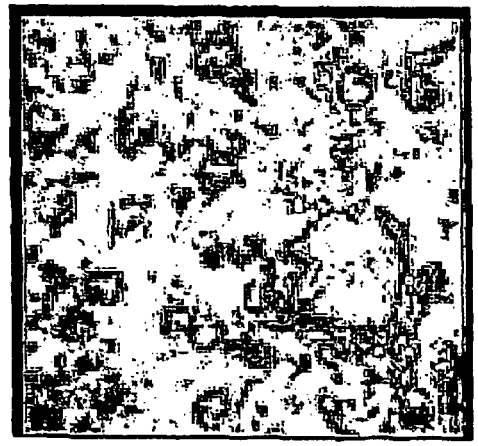
Figure 2D:
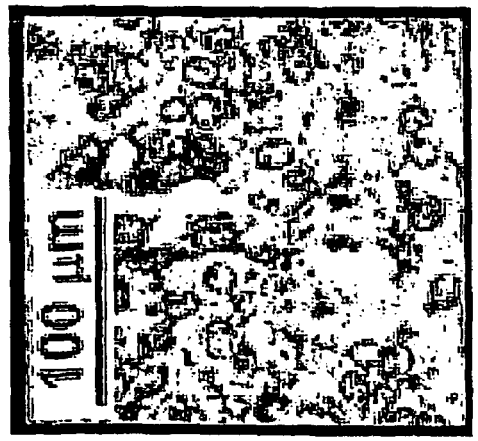

Tumors were dissected 1 hour after PDT, fixed and prepared for IHC. Foci of the ROS-induced LPO product HNE identified by IHC are shown in FIGS. 2D-2F. Photochemical generation of ROS in the course of Pd-Bpheid PDT was confined mainly to the tumor blood vessels, as demonstrated by the anatomic distribution of HNE early after PDT depicted in FIGS. 2D and 2F, in which it is shown that massive generation of HNE adducts co-localized with tumor blood vessels. In tumors taken from light controls (FIGS. 2B, 2E) or dark controls (data not shown), HNE staining was negative in blood vessels and was seen only in necrotic tumor core (spontaneous, PDT independent). FIGS. 2A, 2B and 2C are parallel adjacent sections of 2D, 2E and 2F, respectively, stained with hematoxylin-eosin.

EXAMPLE 3

PDT-induced Hemodynamic Changes

Figure 3G:
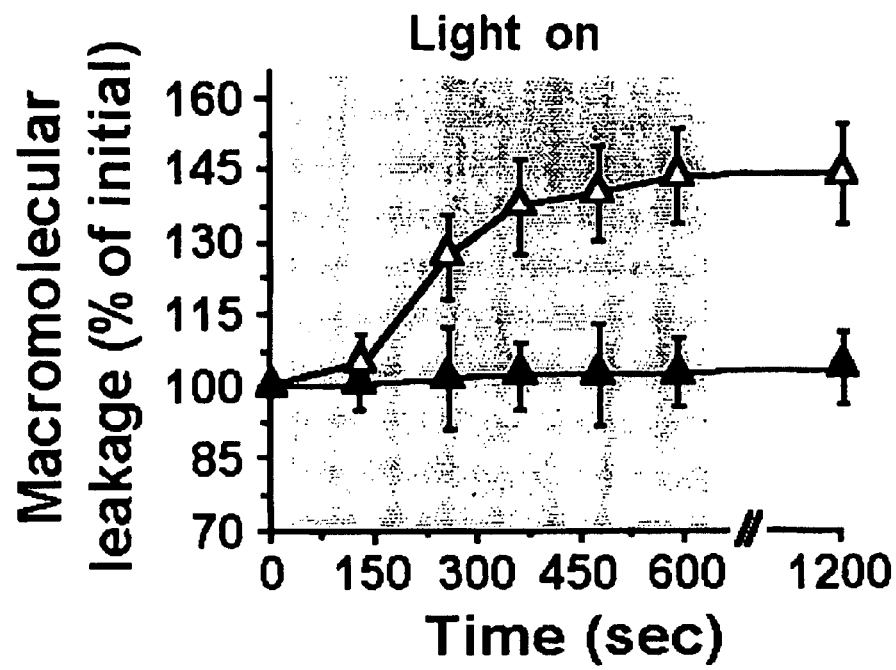

It was reported by us (Zilberstein et al., 2001) and others (Dolmans et al., 2002), that in course of anti-vascular PDT, rapid and intense hemodynamic alterations and stasis are observed in the treated tumor site. In this experiment, fluorescence IVM was used to correlate these hemodynamic changes with the MR signal alterations before, during and after Pd-Bpheid PDT. All IVM experiments were performed on the mouse ear lobe model (Proske et al., 2000), since blood vessels in this area can be easily visualized non-invasively under the microscope. Three hemodynamic parameters were measured: (1) changes in vessel diameter (vasoconstriction), (2) extravascular macromolecular leakage, and (3) red blood cell (RBC) flux. The results are shown in FIGS. 3A-3G. Reduction of about 50% in arteriolar diameter was observed as early as 2-3 minutes after onset of illumination (FIGS. 3A, 3E) concomitant with a sharp decline in blood flow (2-6 minutes after onset of illumination, FIG. 3C), culminating in complete blood stasis (6-7 minutes after onset of illumination, FIG. 3C). Significant changes in vessel diameter or RBC flux were not observed in control animals (FIGS. 3B, D and F). When PDT-induced extravascular leakage of high molecular weight TRITC-dextran (256 KDa) was measured, we observed light-dependent increase in vascular permeability (FIG. 3G), reaching its highest level (145±8% of baseline S.E.) at the end of the illumination period, while extravascular TRITC-dextran leakage in the controls did not exceed 5-7% during the measurement period (20 min, FIG. 3G). Changes in tumor perfusion were assessed before, during and after Pd-Bpheid PDT. Pd-Bpheid administration and immediate illumination of the mouse ear lobe, initiated a rapid decrease in perfusion rate both in arterioles and vennules (open and solid circles, respectively), reaching stasis within 3-4 min (FIG. 3C), while illumination alone had no significant effect (FIG. 3D).

EXAMPLE 4

Hemoglobin (Hb) Saturation in Pd-Bpheid-Photosensitized Blood

Figure 4A:
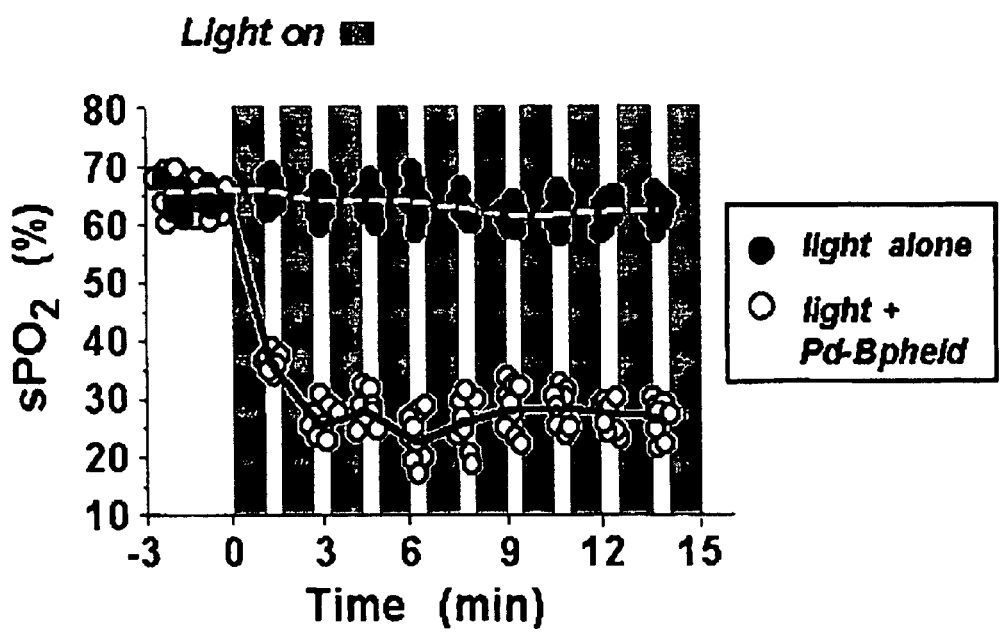
FIGS. 4A-4C show photochemical reduction in sPO$_2$ recorded in human blood using Pd-Bpheid (100 μg/ml) and light (170 mW/cm$^2$). (4A) Spectroscopically: without (solid circles, light alone) or with Pd-Bpheid (open circles, light and Pd-Bpheid). To allow spectroscopic sPO$_2$ measurements, the light was fractionated 10×(1 min light, and 40 sec dark) to enable 8 repetitive 5 sec readings each. Gray and white areas represent light and dark time periods, respectively. (4B, 4C) T2*weighted-MRI. Blood was photosensitized for 1 min ($P_1$, duplicate) and 5 min ($P_5$, duplicate), respectively, and samples were placed separately to minimize the influence of field inhomogeneity. NT, untreated blood; LC, light control (5 min); DC, dark control (duplicate); N$_2$, deoxygenated blood (by N$_2$ equilibration). The above experiments were repeated 3 times.

It was expected that photosensitization of circulating Pd-Bpheid would lead to ROS production with concomitant oxygen depletion. We therefore examined the acute changes in blood oxygenation as manifested by changes in Hb saturation levels (sPO$_2$) using two independent methods:

For spectroscopic examination, fresh human blood was subjected to spectral analysis of sPO$_2$ during PDT in vitro. As shown in FIG. 4A, initial sPO$_2$ (in the dark) was approximately 65% (≦3 min). Upon illumination, a rapid decline in sPO$_2$ was observed reaching a plateau at ~25% (≧2 minutes of illumination). In the absence of Pd-Bpheid, illumination had no effect. These results indicate that photosensitization of Pd-Bpheid in blood leads to a reduction in sPO$_2$.

Figure 4B:
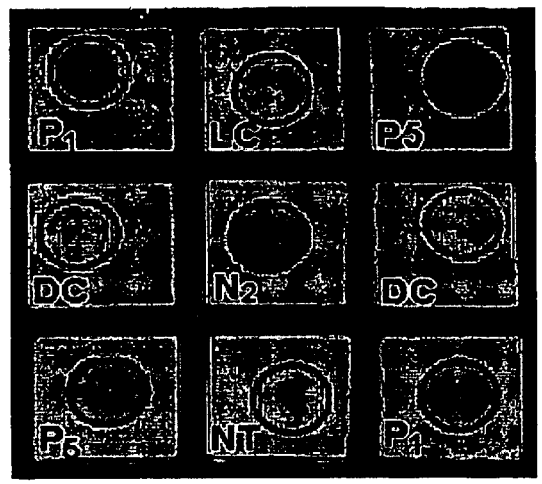
Figure 4C:
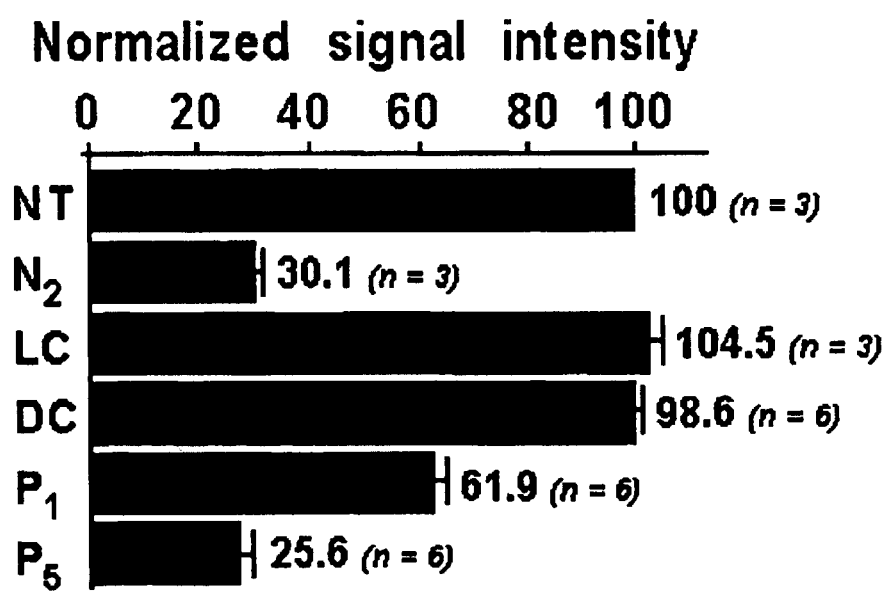

For the MRI examination, we next determined the effect of PDT on sPO$_2$ in isolated human blood, as manifested in T2* weighted MR signal intensity, under similar conditions. MR signal intensity declined by 38.1 and 74.4% following 1 and 5 min illumination, respectively, reaching a basal level equivalent to deoxygenated blood equilibrated with N$_2$ (FIGS. 4B and 4C). Signal intensity of dark and light controls was essentially identical to that of untreated blood, which was defined as 100%. Thus, photosensitization of Pd-Bpheid in blood reduces sPO$_2$ as reflected by a significant decrease in signal intensity of T2 weighted MR images in the absence of flow and volume changes.

EXAMPLE 5

BOLD-contrast MRI During Solid Tumor PDT

Figure 5C:
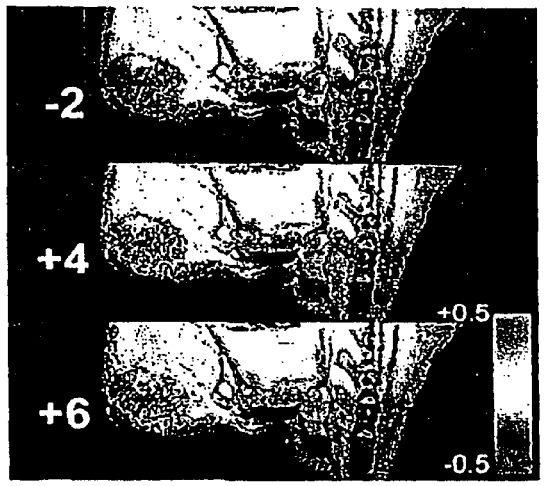
Figure 5D:
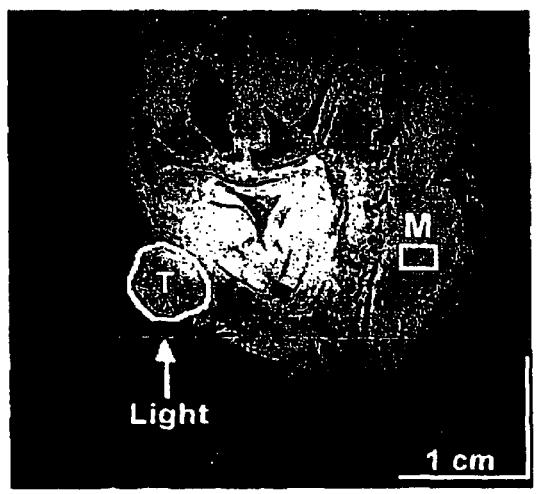
Figure 5E:
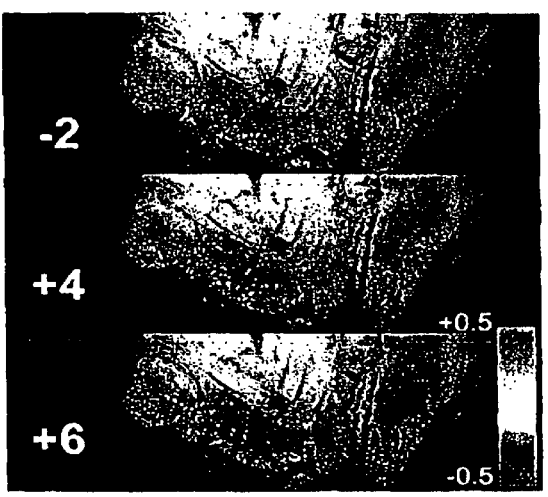
Figures 6A, 6B, 6C:
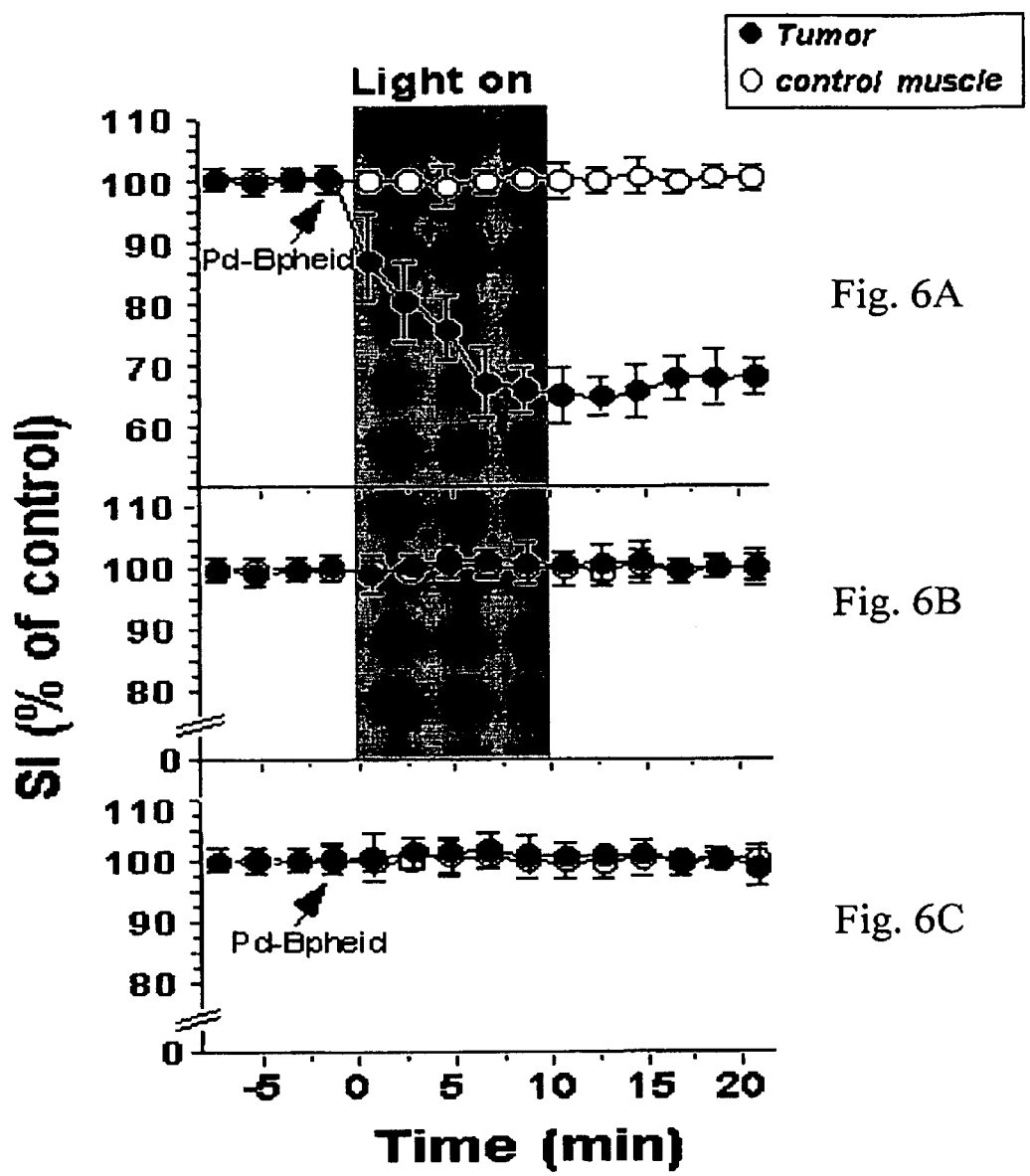
FIGS. 6A-6E are graphs showing the kinetics of changes in two BOLD-contrast MRI parameters (SI and ΔR2*) during Pd-Bpheid-PDT. (6A-6C) Normalized signal intensity (% of baseline at $t_0$±S.E.M.) was calculated from two regions of interest: tumor and unilluminated control muscle as indicated in FIG. 5 (T and M, respectively). (6A): PDT (n=6), (6B): light control (n=4) and (6C): dark control (n=4). (6D, 6E) ΔR2* reflects changes in blood oxygenation and is independent of flow effects. R2* maps were derived by weighted linear regression of ln (SI), from data acquired using multi-echo gradient echo (MEGE). The rapid increase in ΔR2* upon drug administration and illumination (6D) correlates with reduction in SI (6E) in the tumor (n=4). No significant changes in SI or ΔR2* were observed in the light control mouse (n=4). (6D) and (6E) are representative data from the same mouse.
Figures 6D, 6E:
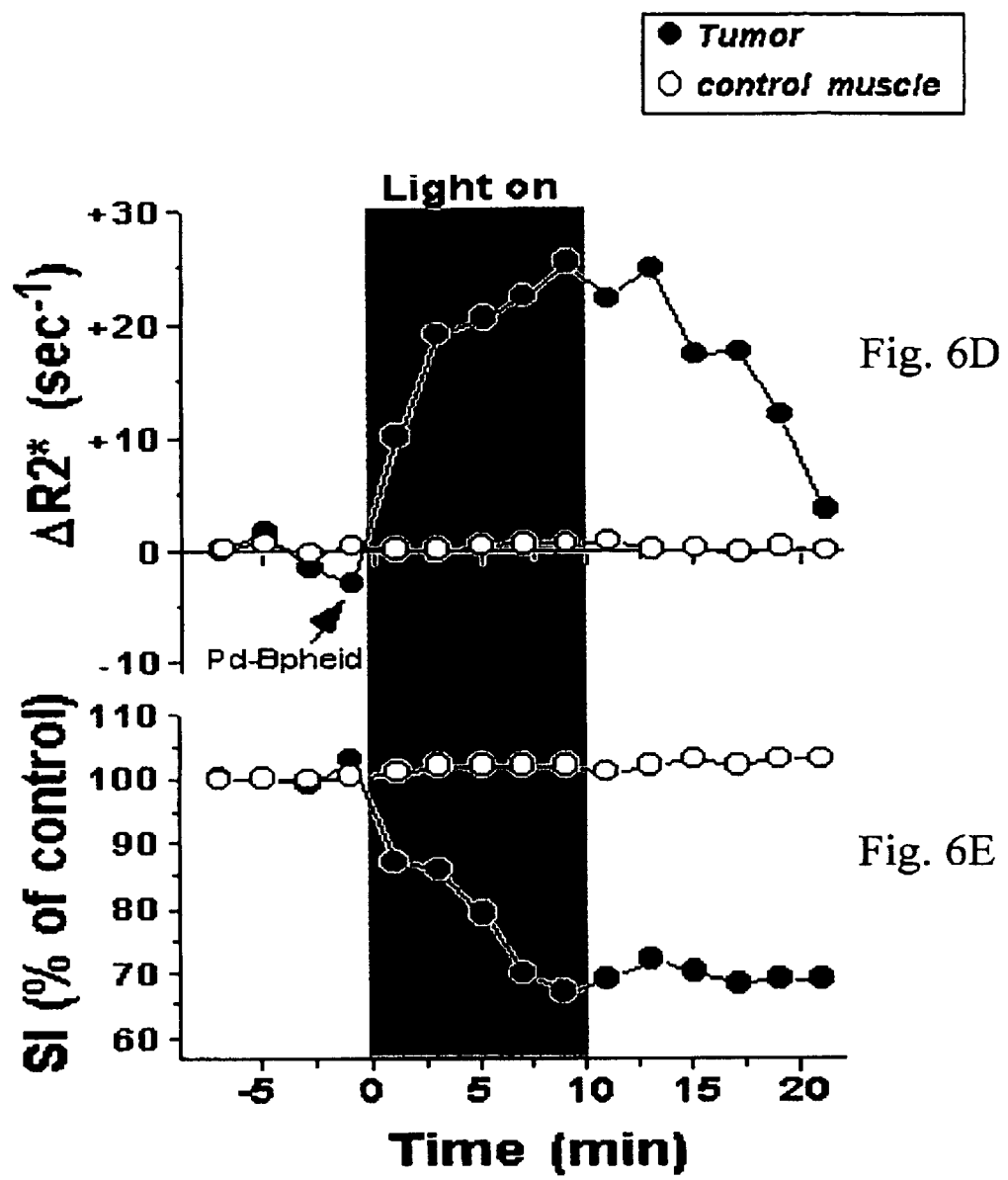

Having shown that photosensitization of Pd-Bpheid induces changes in blood oxygen levels, we next attempted to detect such changes during PDT of a solid tumor in vivo, using MRI. BOLD-MR imaging was applied before, during and after PDT of the solid subcutaneous M2R melanoma tumor. The results are shown in FIGS. 5B-5E and 6A-6E. Pd-Bpheid administration, followed by instant tumor illumination, induced a profound decrease in the MR signal intensity (25-40%) solely within the illuminated tumor area (FIGS. 5C, 6A and 6E). The strongest decrease in MR signal intensity was observed at the tumor rim (FIG. 5C), in good agreement with the spatial pattern of PDT-induced LPO (FIG. 2F). No detectable change in signal intensity (SI) was observed in unilluminated muscle (FIGS. 5C and 6A, open circles) or in the light (FIGS. 5E and 6B) and dark (FIG. 6C) tumor controls. MR signal attenuation developed during the first 6-7 minutes of illumination and remained low throughout the experiment. These results suggest that rapid (≦2 min), local, photosensitized MR BOLD-contrast is generated during PDT. Moreover, it appears that the decline in perfusion rate and MR signal intensity changes exhibit a similar kinetic pattern (FIGS. 6A and 3C), suggesting that vascular shutdown is a major factor contributing to the light dependent changes in MR contrast.

Multiecho gradient echo (MEGE) was suggested as a method to distinguish changes in blood oxygenation from flow effects (Howe et al., 2001). MEGE revealed rapid increase in $\Delta R2^*$ upon photosensitizer administration and illumination (FIG. 6D). This result suggests that the decrease in SI (FIG. 6E) may be attributed, at least in part, to a reduction in blood oxygenation. The MRI value $\Delta R2^*$ (relaxivity difference in T2*-weighted acquisitions) is dependent only on changes in blood oxygenation and volume, and is not dependent on blood flow.

Discussion of the Results

The results obtained according to the present invention demonstrate that intravascular photosensitization of Pd-Bpheid generates a change in MR BOLD-contrast detectable by MRI. As described above, Pd-Bpheid based PDT-of a mouse bearing an M2R melanoma tumor led to a 25-40% decline in MR signal intensity (FIG. 6A), solely confined to the illuminated tumor (FIG. 5C). We suggest that this phenomenon results mainly from two processes that act in concert.

The first process responsible for the decline of the MR signal intensity is the rapid photochemical $O_2$ consumption that takes place within seconds of illumination, leading to a rapid decline in $sPO_2$ (~75% within the first min of illumination, FIG. 4A), as demonstrated by spectral analysis, and by reduced signal intensity in T2*-weighted MR images of blood without changes in flow/volume (74.4% at 5 min of illumination, FIG. 4C). This deoxygenation of Hb was also expected to significantly contribute to changes in bulk magnetic susceptibility, consistent with the changes in T2*-weighted BOLD-contrast observed in vivo (FIGS. 5C, 6A, D and E). These results were consistent with our previous report in which tissue $pO_2$ during PDT was directly measured in the same tumor model using an optical $O_2$ sensor (Zilberstein et al., 1997).

The second process that leads to the drop in the MR signal intensity is associated with the rapid hemodynamic effect manifested by local vascular occlusion and stasis (within minutes), as revealed by IVM (FIG. 3). The first process affects Hb saturation with consequent drop of the MR signal while the second process prevents local reoxygenation, thereby resulting in enhancement of the photochemically-generated MR contrast (Turner, 1997). Reduced blood flow may further attenuate the MR signal by reducing inflow effects ($T_1$ contrast).

Consequently, our results suggest that the observed changes in BOLD-contrast are the result of contributions by both photochemical and hemodynamic effects exclusively reporting from within the blood stream, where photosensitization takes place. The kinetics of the two processes are similar (FIGS. 3C and 4A), but their relative contribution to the overall decline in signal intensity (FIG. 6A) has yet to be established. It thus appears that these two processes are closely related in time and space as judged by independent criteria (BOLD-contrast MRI, LPO-IHC and IVM).

These results describe, for the first time, functional imaging of solid tumors using BOLD-sensitive parameters that may be applied to the online monitoring of clinical PDT. Based on these results, novel intraoperative applications may be suggested for PDT of internal tumors such as prostate, lung, brain, kidney, colon, and other internal tumors. Photosensitized BOLD-contrast MRI may provide accurate 3D-monitoring of tumor vascular insult, the hallmark of antivascular PDT. Furthermore, in the case of internal tumors, where light is interstitially delivered, undesired damage to neighboring organs, nerve bundles or major blood vessels requires precise delivery of light. Thus, the concept of photosensitized functional MRI may be applied for guided light delivery permitting interactive adjustments of light beam direction and intensity. Due to the appreciable depth of Pd-Bpheid photosensitization in vivo (Chen et al., 2002; Koudinova et al., 2003), functional guidance may be effective for a few cm around the interstitial optic fiber. Consequently, this imaging technology may be developed also for obtaining detectable changes in BOLD-contrast in the presence of sub-destructive delivery of attenuated photosensitizer and light doses, prior to the therapeutic treatment. This is feasible since (i) photochemical oxygen depletion is almost instantaneous (FIG. 4A and Zilberstein et al, 1997) and (ii) photosensitized MR BOLD-contrast is of an extremely high magnitude (FIGS. 6A and 6D, about 10-fold higher than reported for physiological activation of brain function (around 5%) (Detre and Floyd, 2001) and comparable to vasoactively induced stimuli affecting BOLD-contrast in tumors as previously reported by us (Abramovitch et al., 1998a, 1998b; Gilead and Neeman, 1999). Consequently, delivery of pulsed light, gated with rapid MRI sequences, may ensure that light will be mostly off during MRI data acquisition, minimizing vascular damage and the potential contribution of downstream spread of deoxygenated blood on the MR-readout. Such a setup will maximize the photochemical and minimize the hemodynamic contributions to MR-contrast.

In view of the fact that intraoperative open-magnet MRI is being widely employed for controlling complex surgical procedures (reviewed in Lipson et al., 2001, and Jolesz, 1998), the results herein indicate that the photosensitized MRI method of the present invention can be applied for real time guidance and assessment of PDT.

REFERENCES

Abramovitch, R., Frenkiel, D. & Neeman, M. Analysis of subcutaneous angiogenesis by gradient echo magnetic resonance imaging. *Magn Reson Med.* 39, 813-824 (1998a).

Abramovitch, R., Marikovsky, M., Meir, G. & Neeman, M. Stimulation of tumor angiogenesis by proximal wounds: spatial and temporal analysis by MRI. *Br J Cancer.* 3, 440-447 (1998b).

Chen, Q., Huang, Z., Luck, D., Bechers, J., Brun, P. H., Wilson, B. C., Scherz, A., Salomon, Y., Hetzel F. W. Preclinical studies in normal canine prostate of a novel Palladium-Bacteriopheophorbide (WST09) photosensitizer for photodynamic therapy of prostate cancer. *Photoch Photobiol.* 76, 88-95 (2002).

Detre, J. A. and Floyd, T. F. Functional MRI and its applications to the clinical neurosciences. *Neuroscientist.* 7, 64-79 (2001).

Dolmans, D. E., Kadambi, A., Hill, J. S., Waters, C. A., Robinson, B. C., Walker, J. P., Fukumura, D., Jain, R. K. Vascular accumulation of a novel photosensitizer, MV6401, causes selective thrombosis in tumor vessels after photodynamic therapy. *Cancer Res.* 62, 2151-2156 (2002).

Dougherty, T. J. An update on photodynamic therapy applications. *J Clin Laser Med Surg.* 20, 3-7 (2002).

Fine, S. L. Photodynamic therapy with verteporfin is effective for selected patients with neovascular age-related macular degeneration. *Arch Ophthalmol.* 117, 1329-1345 (1999).

Fingar., V. H., Kik, P. K., Haydon, P. S., Cerrito, P. B., Tseng, M., Abang, E., Wieman, T. J. Analysis of acute vascular damage after photodynamic therapy using benzoporphyrin derivative (BPD). *Br J Cancer.* 79, 1702-1708 (1999).

Gilead, A. and Neeman, M. Dynamic remodeling of the vascular bed precedes tumor growth: MLS ovarian carcinoma spheroids implanted in nude mice. *Neoplasia.* 1, 226-230 (1999).

Gross, S., Brandis, A., Chen, L., Rosenbach-Belkin, V., Roehrs, S., Scherz, A., Salomon, Y. Protein-A-mediated targeting of bacteriochlorophyll-IgG to *Staphylococcus aureus*: a model for enhanced site-specific photocytotoxicity. *Photochem Photobiol.* 66, 872-878 (1997).

Hopper, C. Photodynamic therapy: a clinical reality in the treatment of cancer. *Lancet Oncol.* 1, 212-219 (2000).

Howe, F. A., Robinson, S. P., McIntyre, D. J., Stubbs, M., Griffiths, J. R. Issues in flow and oxygenation dependent contrast (FLOOD) imaging of tumours. Effects of different levels of hypercapnic hyperoxia on tumour R(2)* and arterial blood gases. *NMR Biomed,* 14, 497-506 (2001).

Jolesz, F. A. Interventional and intraoperative MRI: a general overview of the field. *J Magn Reson Imaging.* 8, 3-7 (1998).

Jordan, B. F., Misson, P., Demeure, R., Baudelet, C., Beghein, N., Gallez, B. Changes in tumor oxygenation/perfusion induced by the NO donor, isosorbide dinitrate, in comparison with carbogen: monitoring by EPR and MRI. *Int J Radiat Oncol Biol Phys.* 48, 565-570 (2000).

Kelleher, D K., Thews, O., Rzeznik, J., Scherz, A., Salomon, Y., Vaupel, P. Water-filtered infrared-A radiation: a novel technique for localized hyperthermia in combination with bacteriochlorophyll-based photodynamic therapy. *Int J Hyperthermia.* 15, 467-474 (1999).

Kokotov S, Lewis A, Neumann R, Amrusi S. X-ray induced visible luminescence of porphyrins. *Photochem Photobiol.* 59. 385-387 (1994).

Koudinova, N., Pinthus, J. H., Brandis, A., Brenner, O., Bendel, P., Ramon J., Eshhar, Z., Scherz, A, Salomon, Y. Photodynamic therapy with Pd-bacteriopheophorbide (TOOKAD): successful in vivo treatment of human prostatic small cell carcinoma xenograft. *Intl. J. Cancer Res.* 104, 782-789 (2003).

Lipson, A C., Gargollo, P C. & Black, P M. Intraoperative magnetic resonance imaging: considerations for the operating room of the future. *J. Clin Neurosci.* 8, 305-310 (2001).

Mansfield, R., Bown, S., McEwan, J. Photodynamic therapy: shedding light on restenosis. *Heart.* 86, 612-618 (2001).

Michelson, S. and Leith, J T. Host response in tumor growth and progression. *Invasion Metastasis.* 16, 235-246 (1996).

Neeman, M., Dafni, H., Bukhari, O., Braun, R D. & Dewhirst, M W. In vivo BOLD contrast MRI mapping of subcutaneous vascular function and maturation: validation by intravital microscopy. *Magn Reson Med.* 45, 887-898 (2001).

Pogue, B W., Braun, R D., Lanzen, J L., Erickson, C., Dewhirst, M W. Analysis of the heterogeneity of pO2 dynamics during photodynamic therapy with verteporfin. *Photochem Photobiol.* 74, 700-706 (2001).

Proske, S., Vollmar, B. & Menger, M D. Microvascular consequences of thrombosis in small venules: an in vivo microscopic study using a novel model in the ear of the hairless mouse. *Thromb Res.* 98, 491-498 (2000).

Rosenbach-Belkin, V. Chen, L., Fiedor, L., Tregub, I., Pavlotsky, F., Brumfeld, V., Salomon, Y., Scherz, A. Serine conjugates of chlorophyll and bacteriochlorophyll: photocytotoxicity in vitro and tissue distribution in mice bearing melanoma tumors. *Photochem Photobiol.* 64, 171-181 (1996).

Schreiber, S., Gross, S., Harmelin, A., Scherz, A., Salomon, Y. Local photodynamic therapy (PDT) of rat C6 glioma xenografts with Pd-Bacteriopheophorbide leads to decreased metastases and increase of animal cure compared to surgery. *Int J Cancer.* 99, 279-285 (2002).

Sibata, C H., Colussi, V C., Oleinick, N L. & Kinsella, T J. Photodynamic therapy in oncology. *Expert Opin Pharmacother.* 2, 917-927 (2001).

Taylor, N J., Baddeley. H., Goodchild, K A., Powell, M E., Thoumine, M., Culver, L A., Stirling, J J., Saunders, M I., Hoskin, P J., Phillips, H., Padhani, A R., Griffiths, J R. BOLD MRI of human tumor oxygenation during carbogen breathing. *J Magn Reson Imaging.* 14, 156-163 (2001).

Turner, R. Signal sources in BOLD contrast fMRI. *Adv Exp Med Biol.* 413, 19-25 (1997).

Uchida, K., Itakura, K., Kawakishi, S., Hiai, H., Toyokuni, S. & Stadtman, ER. Characterization of epitopes recognized by 4-hydroxy-2-nonenal specific antibodies. *Arch Biochem Biophys.* 324, 241-248 (1995).

Zilberstein, J., Schreiber, S., Bloemers, M C W M., Bendel, P., Neeman, M., Schechtman, E., Kohen, F., Scherz, A., Salomon, Y. Antivascular treatment of solid melanoma tumors with bacteriochlorophyll-serine-based photodynamic therapy. *Photochem Photobiol.* 73, 257-266 (2001).

Zilberstein, J., Bromberg, A., Franz, A., Rosenbach-Belkin, V., Kritzmann, A., Pfefermann, R., Salomon, Y., Scherz, A. Light-dependent oxygen consumption in bacteriochlorophyll-serine-treated melanoma tumors: on-line determination using a tissue-inserted oxygen microsensor. *Photochem Photobiol.* 65, 1012-1019 (1997).

The invention claimed is:

1. A method for on-line functional clinical guidance or monitoring and follow-up of treatment progression of a therapeutic modality, optionally during an operation, involving treatment by a blood-borne or interstitial sensitizer using Blood Oxygenation Level-Dependent (BOLD)-magnetic resonance imaging (MRI) wherein said sensitizer, upon excitation by the appropriate sensitizing radiation, initiates local oxygen consumption or depletion thereby inducing a change in BOLD contrast, said method comprising:
   (i) generating a BOLD-weighted MR-image of the target region of interest within the patient's body (time $t_0$);
   (ii) administering said sensitizer to the patient;
   (iii) irradiating the target region of interest within the patient's body with the appropriate sensitizing radiation thereby inducing a change in BOLD contrast, while the patient is placed in the magnetic field of an MRI spectrometer and is subjected to continuous MR imaging;
   (iv) recording said change in BOLD contrast by generating a sole or a plurality of T2* weighted sequential BOLD MR-images during and/or after irradiation (time t);
   (v) processing the data generated at time $t_0$ and time t and generating a BOLD-contrast color-coded difference or ratio map on a pixel by pixel basis; and
   (vi) analyzing the processed data by displaying a composite image obtained by superimposing the BOLD-contrast map generated in (v) on the image generated in (i), wherein areas in said composite image, which show a BOLD contrast effect should coincide with areas treated with said therapeutic modality, thereby providing on line information on said treatment progression.

2. An online BOLD-MRI method according to claim 1, wherein said therapeutic modality is applied to a disease or disorder treatable by local embolization or recanalization.

3. An online BOLD-MRI method according to claim 1, wherein said therapeutic modality is photodynamic therapy (PDT).

4. An online BOLD-MRI method according to claim 3, wherein the sensitizer used in the PDT modality is a photosensitizer excitable by electromagnetic radiation selected from the group consisting of ultraviolet, visible, infrared, and near-infrared light.

5. An online BOLD-MRI method according to claim 3, wherein the sensitizer used in the PDT modality is a photosensitizer directly or indirectly excitable by ionizing radiation.

6. An online BOLD-MRI method according to claim 5, wherein said ionizing radiation is x-ray.

7. An online BOLD-MRI method according to claim 4, wherein said photosensitizer used in PDT, upon excitation by ultraviolet, visible, infrared or near-infrared light, catalyzes photoconversion of oxygen to local cytotoxic Reactive Oxygen Species (ROS).

8. An online BOLD-MRI method according to claim 7, wherein said photosensitizer is a chlorophyll (CHl) or a bacteriochlorophyll (Bchl) compound.

9. An online BOLD-MRI method according to claim 8, wherein said photosensitizer is a metal-substituted Bchl compound.

10. An online BOLD-MRI method according to claim 9, wherein said metal-substituted Bchl compound is palladium-bacteriopheophorbide (Pd-Bpheid) or palladium $3^1$-oxo-15-methoxycarbonylmethyl-rhodobacteriochlorin $13^1$-(2-sulfoethyl)amide potassium salt.

11. An online BOLD-MRI method according to claim 7, wherein said photosensitizer is selected from the group consisting of porfimer, temoporfin, ALA (5-aminolevulinic acid), lutetium texaphyrin, talaporfin and verteporfin.

12. An online BOLD-MRI method according to claims 1, wherein said sensitizer is administered intravenously.

13. An online BOLD-MRI method according to claim 2, wherein said disease or disorder treatable by local embolization is a malignant disease.

14. An online BOLD-MRI method according to claim 13, wherein said malignant disease is breast, prostate, kidney, colon, lung, stomach, bladder, uterus, cervical, ovarian, esophageal, brain or skin cancer.

15. An online BOLD-MRI method according to claim 2, wherein said disease or disorder treatable by local embolization is a non-malignant disease.

16. An online BOLD-MRI method according to claim 15, wherein said non-malignant disease is psoriasis, rheumatoid arthritis, benign prostate hyperplasia, benign mesothelioma, menorrhagia, actinic keratosis, or an ophthalmologic disease.

17. An online BOLD-MRI method according to claim 16, wherein said ophthalmologic disease is age-related macular degeneration.

18. An online BOLD-MRI method according to claim 2, wherein said disease or disorder treatable by local recanalization is a cardiovascular disorder.

19. An online BOLD-MRI method according to claim 18, wherein said cardiovascular disorder is restenosis after angioplasty or atherosclerosis.

20. An online BOLD-MRI method according to claim 1, that is performed intraoperatively for real-time assessment of tumor response to PDT.

21. A method for online functional clinical guidance prior to a therapeutic treatment of a disease or disorder treatable by local embolization or recanalization, by BOLD-MR imaging a diseased region within a patient's body, said therapeutic treatment involving a blood-borne or interstitial electromagnetic radiation-excitable agent (herein designated "sensitizer") which, upon excitation by the appropriate radiation, initiates local oxygen consumption or depletion and a change in BOLD contrast, which comprises administering to the patient subjected to continuous MR imaging while placed in the magnetic field of an MRI spectrometer, a non-therapeutic sub-destructive dose of said sensitizer, irradiating the target diseased region with the appropriate sensitizing radiation, and analyzing the changes in the BOLD-MR contrast generated by oxygen consumption in response to excitation of the sensitizer in the diseased region by comparison with an MR-image of the diseased region generated before administration of the sensitizer.

22. A method according to claim 21, for online functional clinical guidance prior to a PDT therapeutic treatment of a disease or disorder treatable by local embolization or recanalization, by BOLD-MR imaging said diseased region within a patient's body, said treatment involving administration to the patient of a photosensitizer which, upon excitation by the appropriate sensitizing radiation, initiates local oxygen consumption or depletion and a change in BOLD contrast, which comprises administering to the patient subjected to continuous MR imaging while placed in the magnetic field of an MRI spectrometer, a non-therapeutic sub-destructive dose of said photosensitizer, irradiating the target diseased region with the appropriate sensitizing radiation, and analyzing the changes in the BOLD-MRI contrast generated by oxygen consumption or depletion in response to excitation of the sensitizer in the diseased region by comparison with an MR-image of the diseased region generated before administration of the photosensitizer.

23. A method for online monitoring and following up a diseased region of the body in the course of a therapeutic treatment of a disease or disorder treatable by local embolization or recanalization by BOLD-MR imaging said diseased region within a patient's body, said therapeutic treatment involving a blood-borne or interstitial electromagnetic radiation-excitable agent (herein designated "sensitizer") which, upon excitation by the appropriate radiation initiates local oxygen consumption or depletion and a change in BOLD contrast, which comprises administering to a patient subjected to continuous MR imaging while placed in the magnetic field of an MRI spectrometer, a therapeutic dose of said sensitizer, irradiating the target diseased region with the appropriate sensitizing radiation, and analyzing the changes in the BOLD-MRI contrast generated by oxygen consumption in response to excitation of the sensitizer in the diseased region by comparison with an MR-image of the diseased region generated before administration of the sensitizer.

24. A method according to claim 23 for online monitoring and following up a diseased region within a patient's body in the course of a PDT therapeutic treatment of a disease or disorder treatable by local embolization or recanalization by BOLD-MR imaging said diseased region within a patient's body, said treatment involving a photosensitizer which, upon excitation by the appropriate sensitizing radiation, initiates local oxygen consumption or depletion and a change in BOLD contrast, which comprises administering a therapeutic dose of the photosensitizer to the patient subjected to continuous MR imaging while placed in the magnetic field of an MRI spectrometer, irradiating the target diseased region with the appropriate sensitizing radiation, and analyzing the changes in the BOLD-MRI contrast generated by oxygen consumption or depletion in response to excitation of the photosensitizer in the diseased region by comparison with an MR-image of the diseased region generated before administration of the sensitizer.

25. A method according to claim 22, wherein said photosensitizer used in PDT, upon excitation by ultraviolet, visible, infrared or near-infrared light, catalyzes photoconversion of oxygen to local cytotoxic Reactive Oxygen Species (ROS), and said photosensitizer is selected from the group consisting of a chlorophyll (Chl) compound, a bacteriochlorophyll (Bchl) compound, porfimer, temoporfin, ALA (5-aminolevulinic acid), lutetium texaphyrin, talaporfin and verteporfin.

26. A method according to claim 25, wherein said Bchl compound is a metal-substituted Bchl compound.

27. A method according to claim 26, wherein said Bchl derivative is palladium-bacteriopheophorbide (Pd-Bpheid) or palladium $3^1$-oxo-15-methoxy-carbonylmethyl-rhodobacteriochlorin $13^1$-(2-sulfoethyl)amide potassium salt.

28. A method according to claim 21, wherein said disease or disorder treatable by local embolization is a malignant disease.

29. A method according to claim 28, wherein said malignant disease is breast, prostate, kidney, colon, lung, stomach, bladder, uterus, cervical, ovarian, esophageal, brain or skin cancer.

30. A method according to claim 21, wherein said disease or disorder treatable by local embolization is a non-malignant disease.

31. A method according to claim 30, wherein said non-malignant disease is psoriasis, rheumatoid arthritis, benign prostate hyperplasia, benign mesothelioma, menorrhagia, actinic keratosis, or an ophthalmologic disease.

32. A method according to claim 31, wherein said ophthalmologic disease is age-related macular degeneration.

33. A method according to claim 21, wherein said disease or disorder treatable by local recanalization is a cardiovascular disorder.

34. A method according to claim 33, wherein said cardiovascular disorder is restenosis after angioplasty or atherosclerosis.

35. A method according to claim 22, wherein said diseased region within a patient's body is the prostate and the photosensitizer is Pd-Bpheid.

36. A method according to claim 24 wherein said photosensitizer used in PDT, upon excitation by ultraviolet, visible, infrared or near-infrared light, catalyzes photoconversion of oxygen to local cytotoxic Reactive Oxygen Species (ROS) and induces a change in BOLD contrast, and said photosensitizer is selected from the group consisting of a chlorophyll (CHl) compound, a bacteriochlorophyll (Bchl) compound, porfimer, temoporfin, ALA (5-aminolevulinic acid), lutetium texaphyrin, talaporfin and verteporfin.

37. A method according to claim 36, wherein said Bchl compound is a metal-substituted Bchl compound.

38. A method according to claim 37, wherein said Bchl derivative is palladium-bacteriopheophorbide (Pd-Bpheid) or palladium $3^1$-oxo-15-methoxy-carbonylmethyl-rhodobacteriochlorin $13^1$-(2-sulfoethyl)amide potassium salt.

39. A method according to claim 23, wherein said disease or disorder treatable by local embolization is a malignant disease.

40. A method according to claim 39, wherein said malignant disease is breast, prostate, kidney, colon, lung, stomach, bladder, uterus, cervical, ovarian, esophageal, brain or skin cancer.

41. A method according to claim 23, wherein said disease or disorder treatable by local embolization is a non-malignant disease.

42. A method according to claim 41, wherein said non-malignant disease is psoriasis, rheumatoid arthritis, benign prostate hyperplasia, benign mesothelioma, menorrhagia, actinic keratosis, or an ophthalmologic disease.

43. A method according to claim 42, wherein said ophthalmologic disease is age-related macular degeneration.

44. A method according to claim 23, wherein said disease or disorder treatable by local recanalization is a cardiovascular disorder.

45. A method according to claim 44, wherein said cardiovascular disorder is restenosis after angioplasty or atherosclerosis.

46. A method according to claim 24 wherein said diseased region within a patient's body is the prostate and the photosensitizer is Pd-Bpheid.

* * * * *